United States Patent
Jeong et al.

(10) Patent No.: US 12,387,336 B2
(45) Date of Patent: Aug. 12, 2025

(54) APPARATUS AND METHOD FOR SENSORY SUBSTITUTION BASED ON DEPTH-TIME MAPPING

(71) Applicant: Electronics and Telecommunications Research Institute, Daejeon (KR)

(72) Inventors: Chi Yoon Jeong, Daejeon (KR); Moo Seop Kim, Sejong-si (KR); Kyeong Deok Moon, Daejeon (KR); Yun Kyung Park, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 913 days.

(21) Appl. No.: 17/526,525

(22) Filed: Nov. 15, 2021

(65) Prior Publication Data

US 2022/0156937 A1 May 19, 2022

(30) Foreign Application Priority Data

Nov. 16, 2020 (KR) .................. 10-2020-0152887

(51) Int. Cl.
*G06K 9/00* (2022.01)
*A61F 9/08* (2006.01)
(Continued)

(52) U.S. Cl.
CPC .................. *G06T 7/10* (2017.01); *A61F 9/08* (2013.01); *A61H 3/06* (2013.01); *A61H 3/061* (2013.01);
(Continued)

(58) Field of Classification Search
CPC ..... G06T 7/10; G06T 7/11; G06T 7/50; G06T 7/55; G06T 7/593; G06T 7/70;
(Continued)

(56) References Cited

U.S. PATENT DOCUMENTS

| 7,995,055 B1 * | 8/2011 | Ma ................... G06V 10/761 |
| | | 382/154 |
| 8,797,386 B2 * | 8/2014 | Chou ................ H04N 13/239 |
| | | 348/62 |

(Continued)

FOREIGN PATENT DOCUMENTS

| KR | 10-2014-0080740 | 7/2014 |
| KR | 10-2016-0090781 | 8/2016 |
| KR | 10-2017-0082326 | 7/2017 |

*Primary Examiner* — Eric Rush
(74) *Attorney, Agent, or Firm* — KILE PARK REED & HOUTTEMAN PLLC

(57) ABSTRACT

Provided are an apparatus and method for sensory substitution based on depth-time mapping. The apparatus for sensory substitution based on depth-time mapping according to the present invention includes an image segmentation unit configured to generate a plurality of depth images by segmenting three-dimensional (3D) image information based on depth, a sensory substitution unit configured to generate pieces of sensory substitution information by converting at least any one of the plurality of depth images into preset sensory information, a depth-time mapping unit configured to map the sensory substitution information to a time axis based on depth information corresponding to the depth image, and an output unit configured to sequentially output the pieces of sensory substitution information in order mapped to the time axis.

17 Claims, 6 Drawing Sheets

(51) Int. Cl.
  *A61H 3/06*   (2006.01)
  *G06F 3/01*   (2006.01)
  *G06T 7/10*   (2017.01)
  *G06T 7/50*   (2017.01)
  *G06T 7/55*   (2017.01)
  *G06V 10/26*  (2022.01)
  *G09B 21/00*  (2006.01)

(52) U.S. Cl.
  CPC ............... *G06F 3/016* (2013.01); *G06T 7/50* (2017.01); *G06T 7/55* (2017.01); *G06V 10/26* (2022.01); *G09B 21/003* (2013.01); *G09B 21/006* (2013.01); *A61H 2003/063* (2013.01); *G06T 2207/10028* (2013.01)

(58) Field of Classification Search
  CPC ............... G06T 17/00; G06T 2200/04; G06T 2207/10021; G06T 2207/10028; G06T 2207/20021; G06T 2207/20112; G06V 10/20; G06V 10/25; G06V 10/255; G06V 10/26; G06V 20/20; G06V 20/64; A61F 9/08; G06F 3/01; G06F 3/011; G06F 3/016; G06F 3/03; G06F 3/0304; H04N 13/106; H04N 13/128; H04N 13/139; H04N 13/156; H04N 13/161; H04N 13/194; H04N 2013/0074; H04N 2013/0081; H04N 2013/0092; G09B 21/003; G09B 21/006; G09B 21/007; A61H 3/00; A61H 3/06; A61H 3/061; A61H 2003/063; A61H 2003/065; A61M 2021/0005; A61M 2021/0022; A61M 2021/0027; A61N 1/36046
  USPC ....... 382/100, 103, 106, 114, 128, 154, 173, 382/232, 276, 282, 291, 312, 325; 345/156, 419; 715/700–702, 729
  See application file for complete search history.

(56) References Cited

U.S. PATENT DOCUMENTS

| | | | |
|---|---|---|---|
| 10,251,788 B1* | 4/2019 | Phan | A61F 9/08 |
| 10,265,218 B2 | 4/2019 | Rollend et al. | |
| 10,334,202 B1 | 6/2019 | Zhou et al. | |
| 10,359,855 B1* | 7/2019 | Vonikakis | G08B 5/36 |
| 11,185,445 B2* | 11/2021 | Quesada | G06T 7/593 |
| 2007/0016425 A1* | 1/2007 | Ward | G09B 21/003 |
| | | | 704/271 |
| 2012/0092460 A1* | 4/2012 | Mahoney | G06V 20/10 |
| | | | 348/46 |
| 2012/0154531 A1 | 6/2012 | Kim et al. | |
| 2015/0002808 A1 | 1/2015 | Rizzo, III et al. | |
| 2017/0343521 A1 | 11/2017 | Chang et al. | |
| 2019/0332167 A1 | 10/2019 | Chenegros et al. | |
| 2020/0158865 A1* | 5/2020 | Arrabolu | A63F 9/0001 |
| 2021/0043049 A1* | 2/2021 | Moura | G06T 7/70 |

* cited by examiner

APPARATUS AND METHOD FOR SENSORY SUBSTITUTION BASED ON DEPTH-TIME MAPPING

CROSS-REFERENCE TO RELATED APPLICATION

This application claims priority to and the benefit of Korean Patent Application No. 10-2020-0152887, filed on Nov. 16, 2020, the disclosure of which is incorporated herein by reference in its entirety.

BACKGROUND

1. Field of the Invention

The present invention relates to an apparatus and method for sensory substitution based on depth-time mapping.

2. Discussion of Related Art

In sensory substitution apparatuses according to the related art, to substitute and transmit other sensory information for visual information, when various objects are present in images, all of the visual information is converted and transmitted at once, and therefore, pieces of information on various objects are overlapping. As a result, the sensory substitution apparatus according to the related art has a problem in that it is difficult for users to accurately perceive sensory substitution information and feel a sense of distance.

SUMMARY OF THE INVENTION

The present invention is directed to an apparatus and method for sensory substitution based on depth-time mapping capable of effectively transmitting spatial information and object shape information to a user by segmenting visual information according to depth information to generate a plurality of pieces of depth image information, generating pieces of sensory substitution information for each segmented depth image, mapping the generated sensory substitution information to a time axis according to the depth information, and sequentially outputting the pieces of generated sensory substitution information.

According to an aspect of the present invention, there is provided an apparatus for sensory substitution based on depth-time mapping including an image segmentation unit configured to segment three-dimensional (3D) image information based on depth to generate a plurality of depth images, a sensory substitution unit configured to convert at least any one of the plurality of depth images into preset sensory information to generate pieces of sensory substitution information, a depth-time mapping unit configured to map the sensory substitution information to a time axis based on depth information corresponding to the depth image, and an output unit configured to sequentially output the pieces of sensory substitution information in order mapped to the time axis.

The depth-time mapping unit may sequentially map the depth image to the time axis in order of distance corresponding to the depth information.

The output unit may sequentially output the pieces of sensory substitution information in consideration of the order of distance.

The sensory substitution unit may convert the depth image into the sensory information that is at least any one of auditory information and tactile information.

The image segmentation unit may include a density analysis unit configured to calculate an image information density distribution according to the depth of the 3D image information, a depth section determination unit configured to determine a plurality of depth sections having different depths from among all depth sections of the 3D image information according to the image information density distribution, and a depth image generation unit configured to segment the 3D image information into the plurality of depth sections to generate the plurality of depth images.

The depth section determining unit may include a density comparison unit configured to compare the image information density calculated according to the depth of the 3D image information with a reference density, a depth interval calculation unit configured to calculate depth intervals corresponding to the plurality of depth sections according to a difference between the image information density and the reference density, and a depth section setting unit configured to set the plurality of depth sections according to the depth intervals.

The depth-time mapping unit may include a time interval determination unit configured to determine a plurality of time intervals in consideration of at least any one of an interval between the plurality of depth sections and an image information density of a depth image, and a mapping unit configured to map each of the plurality of pieces of depth information to one of the plurality of time intervals.

The sensory substitution unit may include a sensory frequency generator configured to convert location information in the depth image into a frequency and generate a plurality of pieces of sensory frequency information, and a sensory information generation unit configured to synthesize the plurality of pieces of sensory frequency information to generate the sensory information representing shape information of an object in the depth image.

The apparatus for sensory substitution based on depth-time mapping may further include an input unit configured to receive depth selection information for selecting the at least one depth image from among the plurality of depth images, in which the image segmentation unit may extract a depth image corresponding to the depth selection information input by the input unit from among the plurality of depth images, and the output unit may sequentially output the pieces of sensory substitution information in response to the depth selection information.

The output unit may include a mixing ratio calculation unit configured to calculate a mixing ratio of the pieces of sensory substitution information corresponding to adjacent depth images for each time interval in consideration of image information density distributions calculated for each of the plurality of depth images arranged in order of depth, a sensory information mixing unit for mixing the pieces of sensory substitution information corresponding to the adjacent depth images according to the mixing ratio calculated for each time interval to generate pieces of mixed sensory substitution information, and a mixed sensory information output unit configured to sequentially output the pieces of mixed sensory substitution information generated for each time interval.

The plurality of depth images may include a first depth image and a second depth image arranged in the order of depth, the pieces of sensory substitution information may include first sensory substitution information corresponding to the first depth image and second sensory substitution information corresponding to the second depth image, the density distribution calculation unit may include a first density distribution calculation unit configured to calculate a first image information density distribution for the first depth image and a second density distribution calculation unit configured to calculate a second image information density distribution for the second depth image, and the mixing ratio calculation unit may determine a mixing ratio pattern of the second sensory substitution information to be mixed in the first sensory substitution information for a first time interval based on the second image information density distribution and determine a mixing ratio pattern of the first sensory substitution information to be mixed with the second sensory substitution information for a second time interval based on the first image information density distribution.

The sensory information mixing unit may gradually change the mixing ratio of the first sensory substitution information in stages as the first time interval elapses, gradually increase the mixing ratio of the second sensory substitution information as the first time interval elapses, gradually decrease the mixing ratio of the first sensory substitution information as the second time interval elapses, and gradually change the mixing ratio of the second sensory substitution information.

According to an aspect of the present invention, there is provided a method of sensory substitution based on depth-time mapping including (a) segmenting three-dimensional (3D) image information into a plurality of depth images, (b) converting the depth image into sensory information to generate pieces of sensory substitution information, (c) mapping the sensory substitution information to a time axis based on depth information corresponding to the depth image, and (d) sequentially outputting the pieces of sensory substitution information in order mapped to a time axis.

In operation (a), the 3D image information in which a color image matches depth image information may be segmented into the plurality of depth images by analyzing a density according to the distance.

In operation (b), each depth image may be converted into at least any one piece of sensory information among tactile information and auditory information.

In operation (c), the generated sensory substitution information may match the plurality of depth images arranged in the order of depth, and information of a depth section closest to a user may match the time axis in consideration of the depth information corresponding to the depth image.

In operation (d), the pieces of sensory substitution information may be sequentially output in the order mapped to the time axis.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
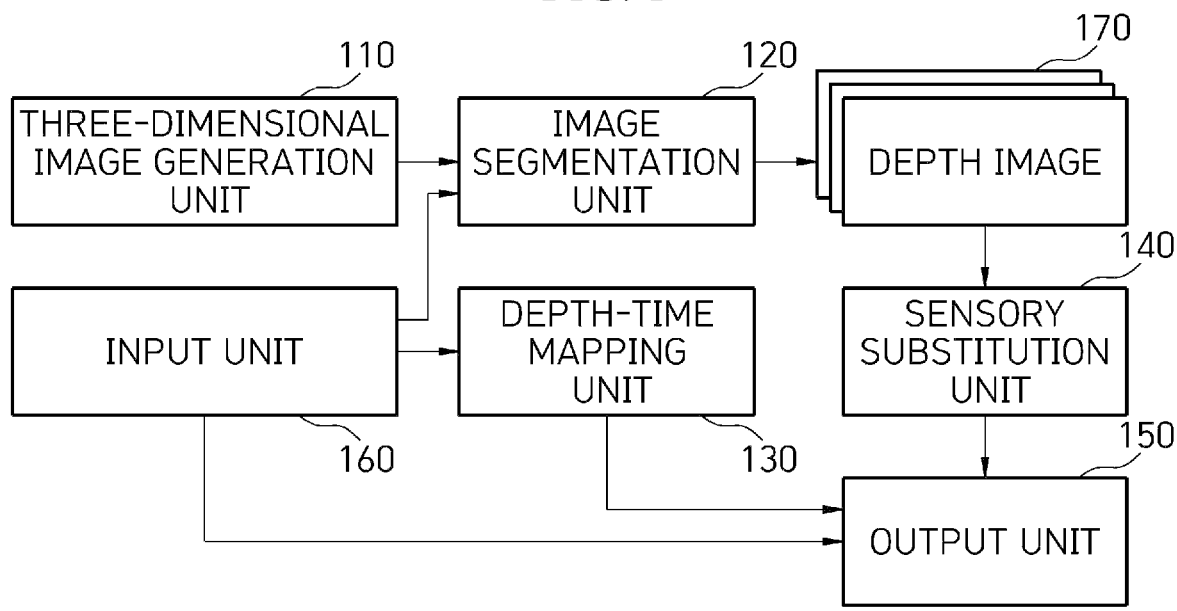
FIG. 1 is a block diagram illustrating a sensory displacement apparatus based on depth-time mapping according to an embodiment of the present invention.

The above-described aspect, and other aspects, advantages, and features of the present invention and methods of accomplishing them will become apparent from the following detailed description of exemplary embodiments with reference to the accompanying drawings.

However, the present invention may be modified in many different forms and it should not be limited to the exemplary embodiments set forth herein. Only the following embodiments are provided to easily inform those of ordinary skill in the art to which the present invention pertains of the object, configuration, and effect of the invention, and the scope of the present invention is defined by the description of the claim.

Meanwhile, terms used in the present specification are for describing exemplary embodiments rather than limiting the present invention. Unless otherwise stated, a singular form includes a plural form in the present specification. Components, steps, operations, and/or elements being described by the terms "comprise" and/or "comprising" used in the present invention do not exclude the existence or addition of one or more other components, steps, operations, and/or elements.

Hereinafter, in order to facilitate the understanding of those skilled in the art, a background in which the present invention is proposed will be first described, and then embodiments of the present invention will be described.

Sensory substitution technology converts and transmits damaged or degraded sensory information into other forms of senses, and thus a user can perceive the sensory information.

Among human sense organs, the amount of information collected through sight accounts for 70% or more of the total amount of information, and the amount of visual information is the largest. As a result, many studies have been conducted on methods to convert and transmit visual information into other alternative senses.

Examples of representative methods include auditory substitution technology that converts and transmit visual information into auditory information, tactile substitution technology that converts and transmits visual information into tactile information, and the like.

The existing auditory and tactile substitution technologies mainly convert color input images into gray images and then convert and transmit the gray images into alternative senses using predefined rules.

The related art converts an input image into a gray image and then maps frequency, amplitude, etc. of sound according to a location and a brightness value of the gray image to generate sound information, groups the same color area in the color image and then maps a color to sound of a musical instrument to convert and transmit the color image into a sound signal, or acquires a depth image, uniformly dividing ten areas in a horizontal direction, and then uses information of each area to generate an acoustic signal.

A real space is expressed in three dimensions, and when three-dimensional (3D) information is mapped to two-dimensional image information using a camera, 3D spatial information is lost.

The sensory substitution methods according to the related art can provide two-dimensional shape information well when converting information into other senses by using two-dimensional image information directly but has a problem in that it is difficult to transmit spatial information (distance information).

Since a human eye perceives the real world, a 3D space, a shape and distance of an object can be recognized at the same time, but the sensory substitution apparatuses according to the related art have a problem in that it is difficult to convey a sense of distance to a user because the information of the color image is mainly converted and transmitted.

In addition, the sensory substitution apparatus according to the related art that substitutes and transmits other forms of sensory information for the visual information converts and transmits the entire visual information into other senses all at once even when a complex image is given as an input, and therefore, pieces of information of various objects are overlapping. As a result, the sensory substitution apparatus according to the related art has a problem in that it is difficult for a user to accurately perceive sensory substitution information.

Since spatial (distance) information is very important in daily life, a method that can transmit shape information and depth information of an object together is required.

The present invention has been proposed to solve the above problems and proposes a method and apparatus for sensory substitution that enables a brain to feel the corresponding sensory information by transmitting information of a person's damaged or degraded senses through other senses based on brain plasticity. Specifically, the present invention proposes an apparatus and method for sensory substitution based on depth-time mapping capable of effectively transmitting spatial information and object shape information to a user by segmenting and generating a plurality of images corresponding to different depths based on depth information, generating sensory substitution information for each segmented depth image, mapping the generated sensory substitution information to a time axis according to the depth information corresponding to the depth image, and sequentially outputting the pieces of generated sensory substitution information.

According to an embodiment of the present invention, since a plurality of depth images are converted into sensory substitution information according to depth information and provided to the user in a time-division manner, by receiving only sensory substitution information of an object present in a specific depth region at a specific time, it is possible for a user to accurately recognize information of an object as compared to the related art, and by mapping pieces of sensory substitution information to the time axis according to the order of distances to sequentially output the pieces of sensory substitution information, it is possible for a user to simultaneously perceive object information and distance information to feel a sense of space.

Hereinafter, in order to help those of ordinary skill in the art understand, auditory substitution technologies for converting visual information, which has significantly more information than other senses, into auditory information, or tactile substitution technologies for converting visual information into tactile sense will be described as an example, but the method of the present invention is not limited to these exemplary senses and may be applied to other sensory information without change.

FIG. 1 is a block diagram illustrating an apparatus for sensory substitution based on depth-time mapping according to an embodiment of the present invention.

The apparatus for sensory substitution based on depth-time mapping according to the embodiment of the present invention includes a three-dimensional (3D) image generation unit 110, an image segmentation unit 120, a depth-time mapping unit 130, a sensory substitution unit 140, an input unit 160, and an output unit 150.

The input unit 160 receives user input such as depth section information and output time information from a user.

The input unit 160 receives user input such as depth section information and output time information preferred by a user and transmits the user input to the image segmentation unit 120, the depth-time mapping unit 130, and the output unit 150 and uses the user input to set a depth section and adjust an output time.

The 3D image generation unit 110 acquires color image information and depth image information using a red/green/blue (RGB) camera and a depth camera (stereo camera, Time-of-Flight (ToF) camera, etc.) and generates a 3D image through image registration and then transmits the generated 3D image to the image segmentation unit 120.

The image segmentation unit 120 analyzes density such as distribution and arrangement of objects present in a 3D image to determine a depth section and segment the objects into depth images of the corresponding depth section.

The image segmentation unit 120 analyzes the density according to the distance using the image information received from the 3D image generation unit 110 to determine the depth section and segments the images of the corresponding depth section to generate the depth images corresponding to each depth section. In this case, the generated depth images are transmitted to the sensory substitution unit and converted into other sensory information such as auditory and tactile information instead of sight.

The sensory substitution unit 140 generates sensory substitution information for each of a plurality of segmented depth images.

The depth-time mapping unit 130 arranges the depth images on the time axis in the order of corresponding distances.

The depth-time mapping unit 130 determines the order, length, etc. in which the sensory substitution unit 140 provides a user with a plurality of pieces of sensory substitution information generated according to the depth section.

The output unit 150 sequentially outputs the sensory substitution information in the order mapped to the time axis.

The output unit 150 sequentially outputs pieces of mixed sensory substitution information generated for each time interval and transmits the mixed sensory substitution information to a user.

Figure 2:
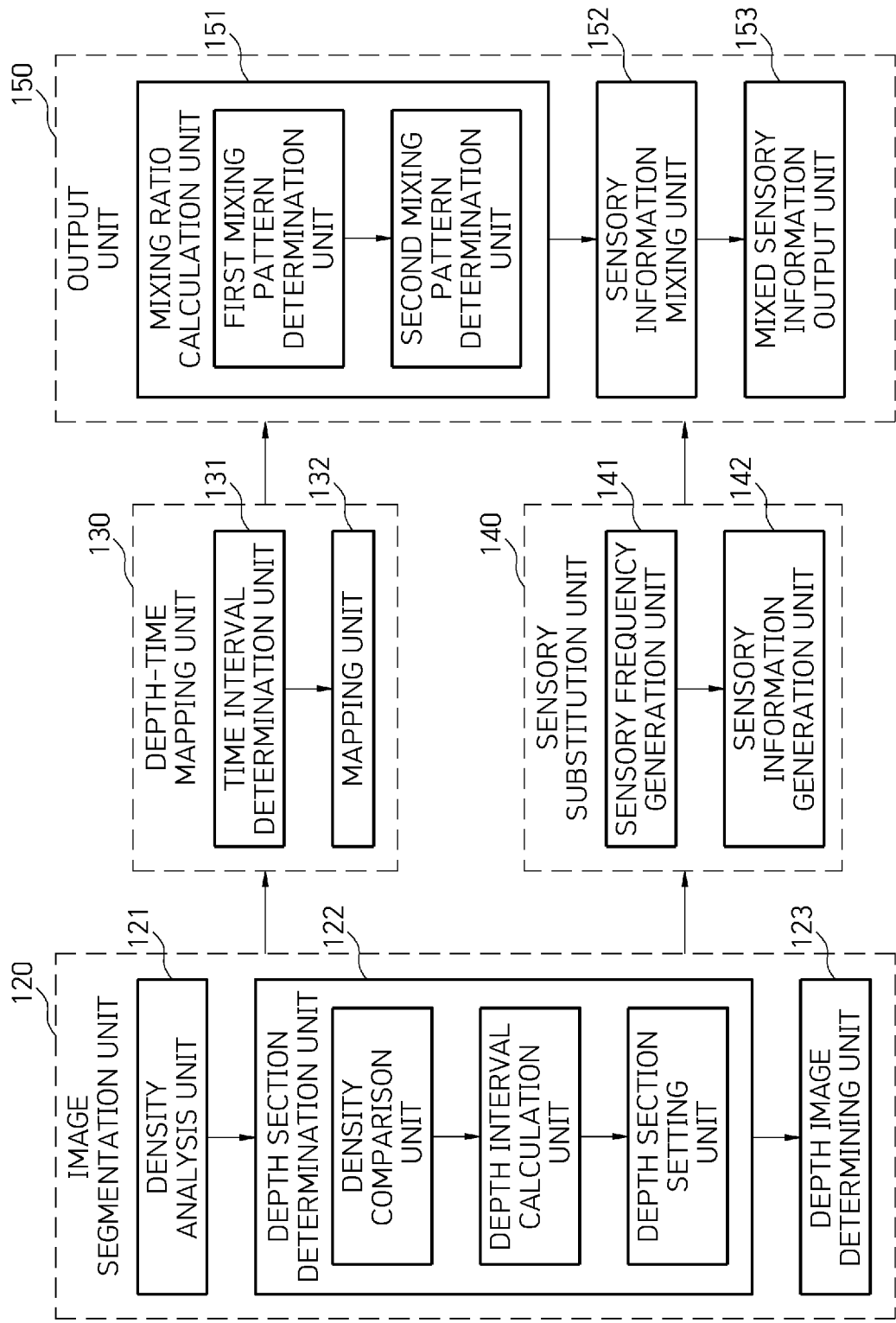
FIG. 2 illustrates detailed configurations of an image segmentation unit, a depth-time mapping unit, a sensory substitution unit, and an output unit of the apparatus for sensory substitution based on depth-time mapping according to the embodiment of the present invention.

FIG. 2 illustrates detailed configurations of the image segmentation unit 120, the depth-time mapping unit 130, the sensory substitution unit 140, and the output unit 150 of the apparatus for sensory substitution based on depth-time mapping according to the embodiment of the present invention.

The image segmentation unit 120 analyzes an image having distance information and color information generated by the 3D image generation unit 110 to calculate density for each distance.

In this case, the density is defined as the number of pixels present at a specific distance, the number of pixels having a predefined characteristic present at a specific distance, and the like.

The predefined characteristics may include a color, texture, a shape, etc. and may include whether or not they belong to a specific object category.

When the densities for each distance are calculated, a density comparison unit included in the depth section determination unit 122 uses statistical characteristics such as an average value, a median value, and a minimum value as a reference density to compare densities of input images.

In this case, a high density of a specific distance means that there are many objects in the corresponding distance, and a low density of a specific distance means that there are few objects in the corresponding distance.

Therefore, it is necessary to apply an adaptive method such as subdividing a depth section for a high-density distance region having a large amount of information to be transmitted and setting a depth section to be wide for a low-density region.

Accordingly, a depth interval calculation unit included in the depth section determination unit 122 analyzes a distribution of density by using the comparison result of the density comparison unit and divides a depth interval.

The depth interval may be divided into uniform intervals or non-uniformly divided by widening a low-density area, narrowly dividing a high-density area, and the like.

The depth interval may be divided using a user's set value transmitted through the input unit.

A depth section setting unit included in the depth section determination unit 122 sets a plurality of depth sections according to the depth interval set by the depth interval calculating unit, and the depth image determining unit 123 generates a plurality of depth images by dividing image information of a corresponding region according to a depth section.

In this case, the plurality of depth images generated at this time may be an RGB image, a depth image, an image in which the depth and the RGB image are matched, or the like.

The sensory substitution unit 140 generates sensory substitution information by using each depth image generated by the image segmentation unit 120.

In the case of substituting auditory information for visual information, the sensory frequency generation unit 141 uses sound components for each vertical position using a frequency defined in a vertical position of an image, time information of a horizontal position, and a brightness value of a pixel to generate sound components for each vertical position, and the sensory information generation unit 142 synthesizes the sound components for each vertical position to generate one sound.

A time interval determination unit 131 of the depth-time mapping unit 130 uses section interval information of the depth section determined by the image segmentation unit 120 to determine a time interval in which the substituted sensory information is transmitted to a user.

When determining the time interval, information such as a length of an output time of the sensory information according to each depth section and the number of depth sections is used.

The time interval in which each piece of substituted sensory information is output may be dynamically set according to the densities of each corresponding depth image.

A relatively short time interval may be set for a depth region having low density, and a relatively long time interval may be set for a depth region having high density.

In addition, the time interval may be divided using the user's set value transmitted through the input unit.

When the time interval is determined by the time interval determination unit 131, the mapping unit 132 maps each of the subdivided and divided depth information to one of a plurality of time intervals.

A mixing ratio calculation unit 151 of the output unit 150 calculates a mixing ratio of pieces of sensory substitution information corresponding to adjacent depth images for each time interval based on the image information density distribution calculated for a plurality of depth images arranged in the order of depth.

When the sensory substitution information generated from the depth image is simply mapped to time and transmitted, a user feels discontinuity in sound, such as a sudden change in sound whenever the depth image changes.

Accordingly, the mixing ratio calculation unit 151 uses densities of a first depth image and a second depth image arranged in the order of depth to determine a mixing ratio of second sensory substitution information when first sensory substitution information is transmitted during a first time interval and determine a mixing ratio of the first sensory substitution information when the second sensory substitution information is transmitted during a second time interval.

When the first sensory substitution information is transmitted during the first time interval, the mixing ratio of the second sensory substitution information transmits only the first sensory substitution information for a certain time and gradually decreases the mixing ratio of the first sensory substitution information and increases the mixing ratio of the second sensory substitution information.

During the initial section of the second time interval, the mixing ratio of the second sensory substitution information gradually increases, and the mixing ratio of the first sensory substitution information gradually decreases.

During a second half period in which the output of the first sensory substitution information becomes less than a reference value in the second time interval, the mixing ratio of the pieces of sensory substitution information is adjusted over time so that the mixing ratio of the second sensory substitution information gradually decreases and a mixing ratio of third sensory substitution information corresponding to a third depth image gradually decreases.

As a result, a user may feel less discontinuity in sound even when the sensory substitution information is changed as the time interval changes.

The mixing ratio may be determined differently depending on the length of the time interval, the density, a difference in sound between the first time interval and the second time interval, etc., and the sum of the mixing ratio of the first time interval and the mixing ratio of the second time interval is always one.

The sensory information mixing unit 152 mixes sensory information using a mixing ratio pattern set by a first mixing pattern determining unit and a second mixing pattern determining unit of the mixing ratio calculation unit 151.

The generated mixed sense is transmitted to a user through the mixed sensory information output unit.

When mixing and generating sensory information generated from depth images arranged in the order of depth, the sensory information mixing unit 152 may additionally use the information generated by the mixing ratio set by the first mixing pattern determiner and the second mixed pattern determiner to adjust a volume level to be output to a user can be adjusted by additionally using the distance information.

For example, by increasing the volume level in the case of mixed information present at a close distance and decreasing the volume level in the case of mixed information present at a far distance, a user may intuitively perceive the sensory substitution information and the distance information based on the time and volume level.

Figure 3:
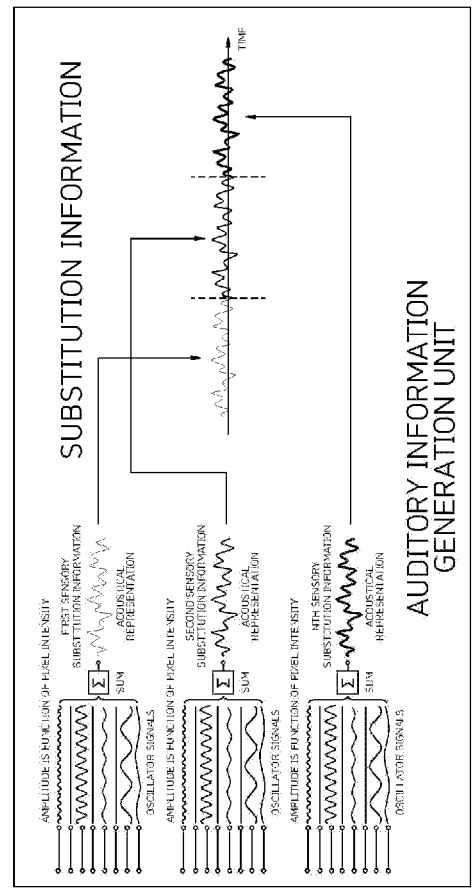
FIG. 3 is a conceptual diagram for generation of auditory information by the apparatus for sensory substitution based on depth-time mapping according to the embodiment of the present invention.
Figure 3:
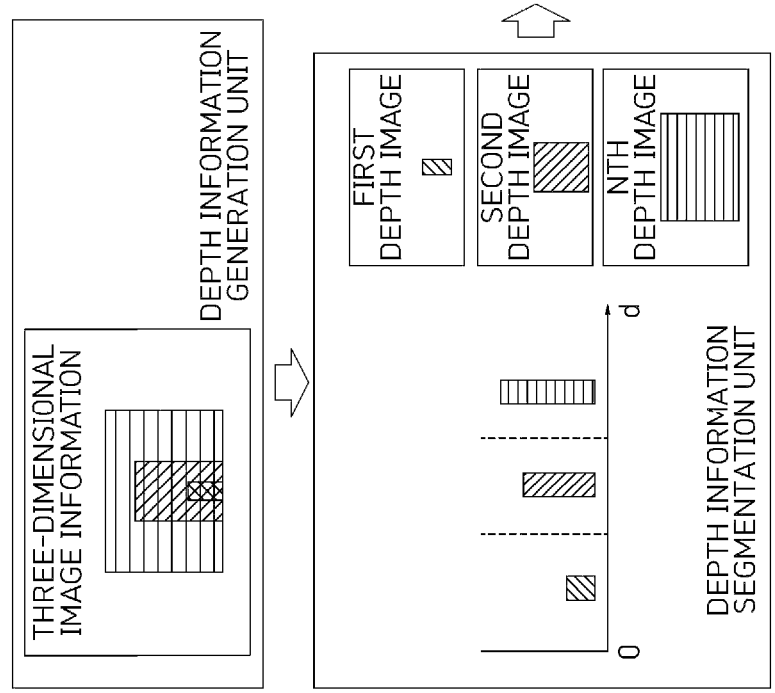

FIG. 3 is a conceptual diagram for the generation of the auditory information by the apparatus for sensory substitution based on depth-time mapping according to the embodiment of the present invention.

Referring to FIG. 3, when 3D image information is generated by matching a color image and a depth image, the density is analyzed based on the number of pixels present according to a distance d.

When there is the distribution of density according to the distance, the distribution of density is analyzed and the 3D image information is segmented into N depth images.

Referring to FIG. 3, three depth sections are set according to the density analysis result and three depth images are generated.

The sensory substitution information is generated using each of the generated depth images, and each piece of generated sensory substitution information is mapped to the time axis and transmitted to a user.

Assuming that the three depth sections are a close distance, a medium distance, and a far distance, a user may naturally perceive that the first sensory substitution information he/she hears is an object that is present at a close distance, the second sensory substitution information he/she hears is an object that is present at a medium distance, and the last sensory substitution information he/she hears is an object that is present at a far distance.

In addition, by dividing the complex image into three areas and transmitting the complex image, it is possible for a user to more accurately recognize shape information of objects at each distance.

Figure 4:
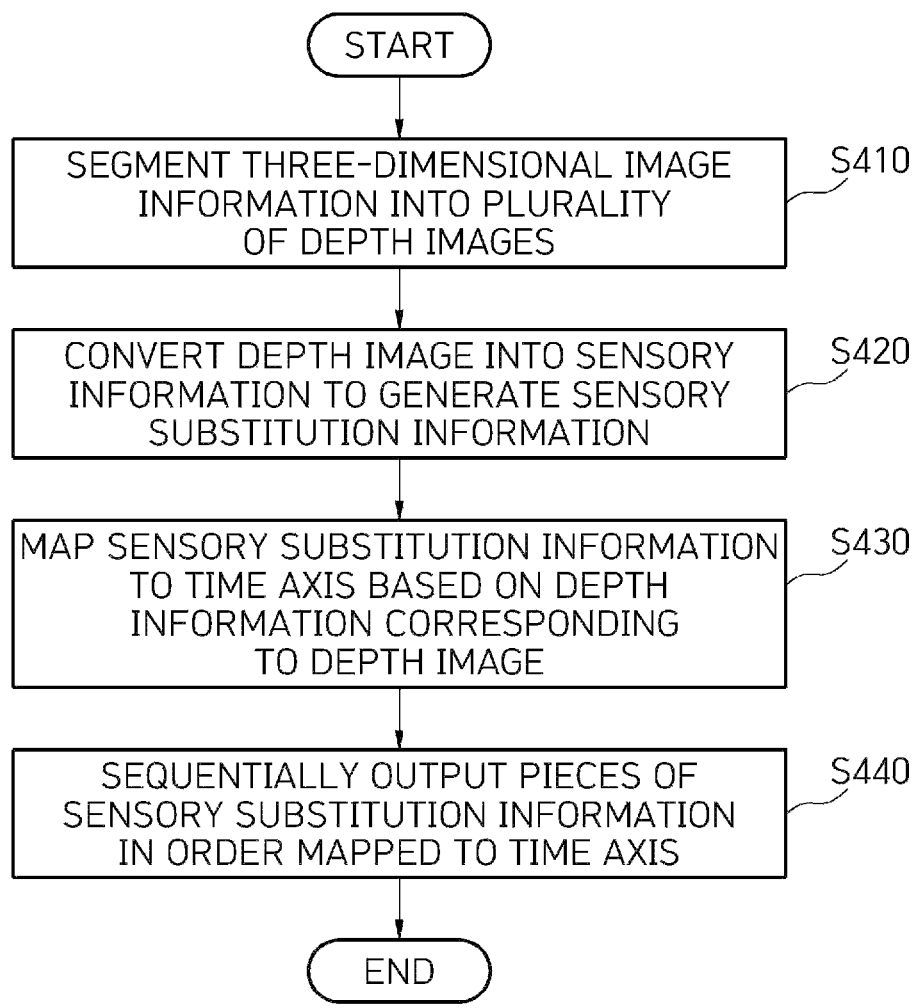
FIG. 4 is a flowchart illustrating a method of sensory substitution based on depth-time mapping according to an embodiment of the present invention.

FIG. 4 is a flowchart illustrating a method of sensory substitution based on depth-time mapping according to an embodiment of the present invention.

The method of sensory substitution based on depth-time mapping according to an embodiment of the present invention includes segmenting three-dimensional (3D) image information into a plurality of depth images (S410), generating pieces of sensory substitution information by converting the depth image into sensory information (S420), mapping the sensory substitution information to a time axis based on depth information corresponding to the depth image (S430), and sequentially outputting the pieces of sensory substitution information in order mapped to a time axis (S440).

In operation S410, the 3D image information in which a color image matches depth image information is segmented into the plurality of depth images by analyzing a density according to the distance.

In operation S420, pieces of sensory substitution information for converting each depth image into other sensory information are generated.

In operation S430, the pieces of generated sensory substitution information match the plurality of depth images arranged in the order of depth, and information of a depth section closest to a user preferentially matches the time axis based on the depth information corresponding to the depth image.

In operation S440, the pieces of sensory substitution information are sequentially output in the order mapped to the time axis.

Figure 5:
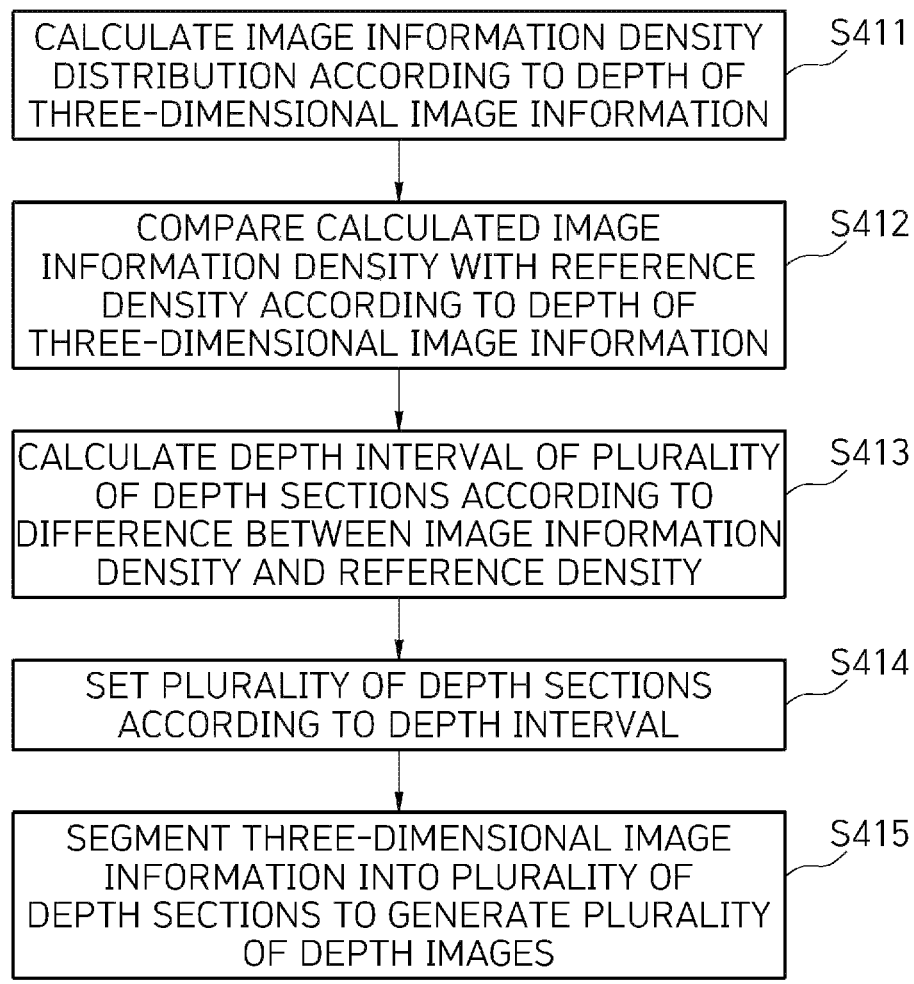
FIG. 5 illustrates a process of determining an image segmentation section according to an embodiment of the present invention.

FIG. 5 illustrates a process of determining an image segmentation section according to an embodiment of the present invention.

In operation S411, the density of the image information according to the depth is calculated using the depth information, the color information, or the like of the 3D image.

In operation S412, the density of image information calculated according to the depth of the image is compared with a reference density calculated from the statistical distribution characteristics of the density, and in operation S413, the depth interval is calculated.

In operation S414, a plurality of depth sections are set using the depth interval, and in operation S415, the input image is divided into the set depth sections to generate a plurality of depth images.

Figure 6:
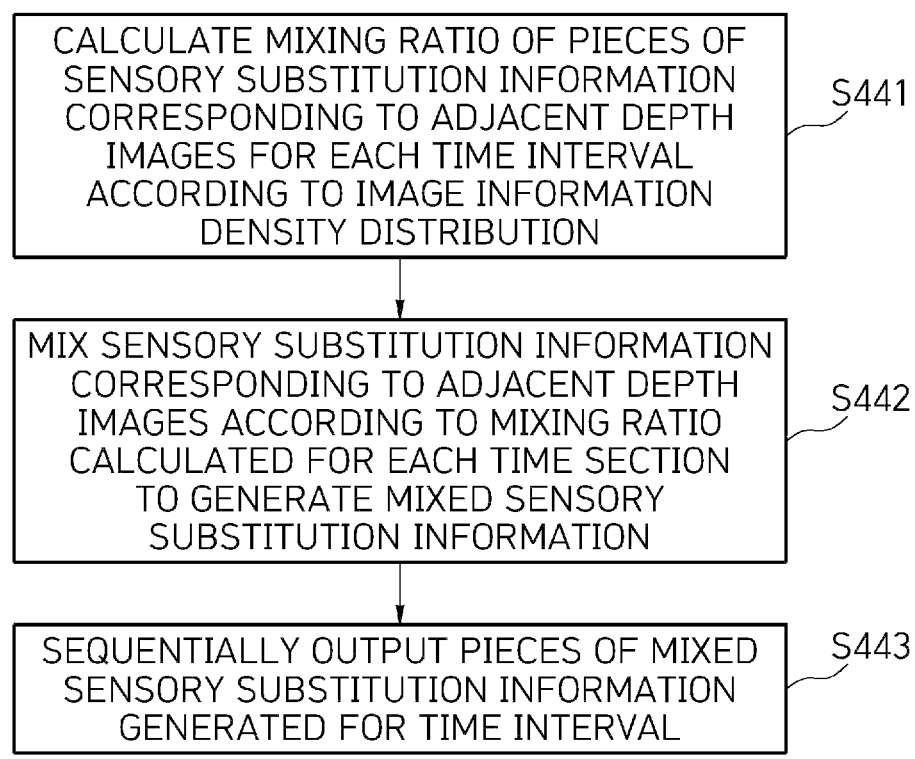
FIG. 6 illustrates a process of outputting sensory substitution information according to an embodiment of the present invention.

FIG. 6 illustrates a process of outputting sensory substitution information according to an embodiment of the present invention.

In operation S441, when the sensory substitution information of a plurality of depth images arranged in the order of depth is input, the mixing ratios for each time interval are calculated according to the density distribution of the image information.

When the sensory substitution information suddenly changes, since a user may experience discomfort due to the sudden change in sound, in order to give an effect such as fade in/fade out, when the time interval ends, it is possible to generate the mixing ratio such as decreasing the mixing ratio of the sensory substitution information of the corresponding section and increasing the mixing ratio of the next time interval.

In addition, in the case of the depth section, which is considered to be important, because of the high-density distribution, more time intervals are allocated or the mixing ratio is adjusted higher than the information of other depth sections.

In operation S442, as the mixing ratio of the sensory substitution information is determined, the sensory substitution information according to time is generated according to the mixing ratio.

In operation S443, the pieces of mixed sensory information generated for each time interval are sequentially output and transmitted to a user.

Meanwhile, the method of sensory substitution based on depth-time mapping according to the embodiment of the present invention may be implemented in a computer system or recorded on a recording medium. The computer system may include at least one processor, a memory, a user input device, a data communication bus, a user output device, and storage. Each of the above-described components performs data communication through the data communication bus.

The computer system may further include a network interface coupled to a network. The processor may be a central processing unit (CPU) or a semiconductor device that processes instructions stored in the memory and/or storage.

The memory and storage may include various types of volatile or non-volatile storage media. For example, the memory may include a read only memory (ROM) and a random access memory (RAM).

Meanwhile, the method of sensory substitution based on depth-time according to the embodiment of the present invention may be implemented by a computer-executable method. When the method of sensory substitution based on depth-time mapping according to the embodiment of the present invention is performed in a computer device, computer-readable instructions may execute the method of sensory substitution based on depth-time mapping according to the present invention.

On the other hand, the method of sensory substitution based on depth-time mapping according to the present invention described above can be implemented as a computer-readable code on a computer-readable recording medium. The computer-readable recording medium includes any type of recording medium in which data readable by a computer system is stored. For example, there may be a ROM, a RAM, a magnetic tape, a magnetic disk, a flash memory, an optical data storage device, and the like. In addition, the computer-readable recording medium may be distributed in computer systems connected through a computer communication network and stored and executed as readable codes in a distributed manner.

According to the present invention, by receiving only sensory substitution information of an object present in a specific depth region at a specific time, it is possible for a user to accurately recognize information of an object as compared to the related art, and by mapping pieces of sensory substitution information to the time axis according to the order of distances to sequentially output the pieces of sensory substitution information, it is possible for a user to simultaneously perceive object information and distance information to feel a sense of space.

The effects of the present invention are not limited to those described above, and other effects not described can be clearly understood by those skilled in the art from the above detailed description.

What is claimed is:

1. An apparatus for sensory substitution based on depth-time mapping, comprising:
    an image segmentation unit configured to segment three-dimensional (3D) image information based on depth to generate a plurality of depth images;
    a sensory substitution unit configured to convert plurality of depth images into preset sensory information to generate pieces of sensory substitution information;
    a depth-time mapping unit configured to map the pieces of sensory substitution information to a plurality of time intervals of a time axis based on depth information corresponding to the plurality of depth images; and
    an output unit configured to sequentially output the pieces of sensory substitution information in an order mapped to the time axis,
    wherein the output unit includes:
    a mixing ratio calculation unit configured to calculate a mixing ratio of the pieces of sensory substitution information corresponding to adjacent depth images for each time interval of the plurality of time intervals in consideration of image information density distributions calculated for each of the plurality of depth images arranged in order of depth;
    a sensory information mixing unit for mixing the pieces of sensory substitution information corresponding to the adjacent depth images according to the mixing ratio calculated for each time interval to generate pieces of mixed sensory substitution information, and
    wherein, for each time interval of the plurality of time intervals, the sensory information mixing unit gradually increases and decreases the mixing ratio calculated for the time interval as the time interval elapses.

2. The apparatus of claim 1, wherein the depth-time mapping unit sequentially maps the plurality of depth images to the time axis in order of distance corresponding to the depth information.

3. The apparatus of claim 2, wherein the output unit sequentially outputs the pieces of sensory substitution information in consideration of the order of distance.

4. The apparatus of claim 1, wherein the sensory substitution unit converts the plurality of depth images into the preset sensor information that is at least any one of auditory information and tactile information.

5. The apparatus of claim 1, wherein the image segmentation unit includes:
    a density analysis unit configured to calculate an image information density distribution according to the depth of the 3D image information;
    a depth section determination unit configured to determine a plurality of depth sections having different depths from among all depth sections of the 3D image information according to the image information density distribution; and
    a depth image generation unit configured to segment the 3D image information into the plurality of depth sections to generate the plurality of depth images.

6. The apparatus of claim 5, wherein the depth section determination unit includes:
    a density comparison unit configured to compare an image information density calculated according to the depth of the 3D image information with a reference density;
    a depth interval calculation unit configured to calculate depth intervals corresponding to the plurality of depth sections according to a difference between the image information density and the reference density; and
    a depth section setting unit configured to set the plurality of depth sections according to the depth intervals.

7. The apparatus of claim 5, wherein the depth-time mapping unit includes:
    a time interval determination unit configured to determine the plurality of time intervals in consideration of at least any one of an interval between the plurality of depth sections and an image information density of a depth image; and
    a mapping unit configured to map each of the pieces of sensory substitution information to one of the plurality of time intervals.

8. The apparatus of claim 1, wherein the sensory substitution unit includes:
    a sensory frequency generator configured to convert location information in a depth image of the plurality of depth images into a frequency and generate a plurality of pieces of sensory frequency information; and
    a sensory information generation unit configured to synthesize the plurality of pieces of sensory frequency information to generate sensory information representing shape information of an object in the depth image.

9. The apparatus of claim 1, further comprising an input unit configured to receive depth selection information for selecting a depth image from among the plurality of depth images,
    wherein the image segmentation unit extracts the depth image corresponding to the depth selection information input by the input unit from among the plurality of depth images, and
    the output unit sequentially outputs the pieces of sensory substitution information in response to the depth selection information.

10. The apparatus of claim 1, wherein the output unit includes:
a mixed sensory information output unit configured to sequentially output the pieces of mixed sensory substitution information generated for each time interval of the plurality of time intervals.

11. The apparatus of claim 10, wherein the plurality of depth images include a first depth image and a second depth image arranged in the order of depth,
the pieces of sensory substitution information include first sensory substitution information corresponding to the first depth image and second sensory substitution information corresponding to the second depth image,
a density distribution calculation unit includes a first density distribution calculation unit configured to calculate a first image information density distribution for the first depth image and a second density distribution calculation unit configured to calculate a second image information density distribution for the second depth image, and
the mixing ratio calculation unit determines a mixing ratio pattern of the second sensory substitution information to be mixed in the first sensory substitution information for a first time interval based on the second image information density distribution and determines a mixing ratio pattern of the first sensory substitution information to be mixed with the second sensory substitution information for a second time interval based on the first image information density distribution.

12. The apparatus of claim 11, wherein the sensory information mixing unit gradually changes the mixing ratio of the first sensory substitution information in stages as the first time interval elapses, gradually increases the mixing ratio of the second sensory substitution information as the first time interval elapses, gradually decreases the mixing ratio of the first sensory substitution information as the second time interval elapses, and gradually changes the mixing ratio of the second sensory substitution information.

13. A method of sensory substitution based on depth-time mapping, comprising:
(a) segmenting three-dimensional (3D) image information into a plurality of depth images;
(b) converting the plurality of depth images into sensory information to generate pieces of sensory substitution information;
(c) mapping the pieces of sensory substitution information to a plurality of time intervals of a preset time axis based on depth information corresponding to the plurality of depth images; and
(d) sequentially outputting the pieces of sensory substitution information in an order mapped to the preset time axis,
wherein, in operation (d),
a mixing ratio of the pieces of sensory substitution information corresponding to adjacent depth images for each time interval of the plurality of time intervals is calculated in consideration of image information density distributions calculated for each of the plurality of depth images arranged in order of depth,
pieces of mixed sensory substitution information are generated by mixing the pieces of sensory substitution information corresponding to the adjacent depth images according to the mixing ratio calculated for each time interval of the plurality of time intervals,
and, for each time interval of the plurality of time intervals, the mixing ratio calculated for the time interval is gradually increased and decreased as the time interval elapses.

14. The method of claim 13, wherein, in operation (a), the 3D image information, in which a color image matches depth image information, is segmented into the plurality of depth images by analyzing a density according to a distance.

15. The method of claim 13, wherein, in operation (b), each depth image of the plurality of depth images is converted into at least any one piece of sensory information among tactile information and auditory information.

16. The method of claim 13, wherein, in operation (c), the generated pieces of sensory substitution information match the plurality of depth images arranged in the order of depth, and information of a depth section closest to a user preferentially matches the preset time axis in consideration of depth information corresponding to the depth section.

17. The method of claim 13, wherein, in operation (d), the pieces of sensory substitution information is sequentially output in the order mapped to the preset time axis.

* * * * *